United States Patent
West et al.

(10) Patent No.: US 7,623,679 B2
(45) Date of Patent: Nov. 24, 2009

(54) TEMPORAL SMOOTHING OF A DEFORMATION MODEL

(75) Inventors: Jay B. West, Mountain View, CA (US); Calvin R. Maurer, Jr., Mountain View, CA (US)

(73) Assignee: Accuray Incorporated, Sunnyvale, CA (US)

( * ) Notice: Subject to any disclaimer, the term of this patent is extended or adjusted under 35 U.S.C. 154(b) by 211 days.

(21) Appl. No.: 11/638,827

(22) Filed: Dec. 13, 2006

(65) Prior Publication Data

US 2008/0144908 A1   Jun. 19, 2008

(51) Int. Cl.
 *G06K 9/00* (2006.01)
(52) U.S. Cl. .................................. 382/103; 382/128
(58) Field of Classification Search ................ None
 See application file for complete search history.

(56) References Cited

U.S. PATENT DOCUMENTS

| | | | |
|---|---|---|---|
| 5,189,687 A | 2/1993 | Bova et al. | |
| 5,207,223 A | 5/1993 | Adler | |
| 6,169,817 B1* | 1/2001 | Parker et al. | 382/131 |
| 6,266,062 B1* | 7/2001 | Rivara | 345/419 |
| 6,307,914 B1* | 10/2001 | Kunieda et al. | 378/65 |
| 2003/0072479 A1 | 4/2003 | Totterman et al. | |
| 2004/0034301 A1 | 2/2004 | Falco | |
| 2004/0258286 A1 | 12/2004 | Salla et al. | |
| 2005/0027194 A1 | 2/2005 | Adler et al. | |
| 2005/0084140 A1* | 4/2005 | Kakadiaris et al. | 382/118 |
| 2005/0143651 A1 | 6/2005 | Vernard et al. | |
| 2007/0076846 A1 | 4/2007 | Ruchala et al. | |
| 2007/0167784 A1 | 7/2007 | Shekhar et al. | |

FOREIGN PATENT DOCUMENTS

WO    WO 03/076003    9/2003

OTHER PUBLICATIONS

Coste-Maniére, É., "Robotic whole body stereotacitc radiosurgery: clinical advantages of the CyberKnife® integrated system", The International Journal of Medical Robotics +Computer Assisted Sugery, 2005, www.roboticpublications.com, 14 pages.

Paul Keall, "4-Dimensional Computed Tomography Imaging and Treatment Planning", Seminars in Radiation Oncology, vol. 14, No. 1 (Jan.), 2004, pp. 81-90.

(Continued)

*Primary Examiner*—Brian P Werner
*Assistant Examiner*—Claire Wang
(74) *Attorney, Agent, or Firm*—Blakely, Sokoloff, Taylor & Zafman LLP

(57) ABSTRACT

A method and apparatus for approximating a path of movement of a target. The method includes referencing a temporal sequence of images, identifying a plurality of data points associated with a selected volume element of the volume of interest, and calculating an estimated location of the selected volume element based on a cost function having a constraint which favors continuous spatial motion of the selected volume element over time. Each of the images of the temporal sequence of images depicts a volume of interest. Each of the plurality of data points corresponds to one of the images.

38 Claims, 11 Drawing Sheets

OTHER PUBLICATIONS

Yuichiro Kamino, M.S., et al., "Development of a Four-Dimensional Image-Guided Radiotherapy System with a Gimbaled X-Ray Head", Int. J. Radiation Oncology Biol. Phys., vol. 66, No. 1, 2006, pp. 271-278.

Jay B. West, et al., "Hybrid Point-and-Intensity-Based Deformable Registration for Abdominal CT Images", Medical Imaging 2005: Image Processing, edited by J. Michael Fitzpatrick, Joseph M. Reinhardt, Proc. Of SPIE Vo. 5747 (SPIE, Bellingham, WA, 2005), 1605-7422/05, pp. 204-211.

Rietzel E. et al., "Four-dimensional image-based treatment planning: Target volume segmentation and dose calculation in the presence of respiratory motion", International Journal of Radiation: Oncology Biology Physics, Pergamon Press, US, vol. 61, No. 5, Apr. 1, 2005, pp. 1535-1550, XP004842268, ISSN: 0360-3016.

European Search Report, EP07115355, Dec. 4, 2007, 2 pages.

PCT International Search Report and Written Opinion of the International Searching Authority, PCT/US07/21789 filed Oct. 12, 2007, mailed Sep. 22, 2008.

Communication pursuant to Article 94(3) mailed Oct. 30, 2008, for EP application No. 07115355.5.

Jay B. West, Calvin R. Maurer, Jr., John R. Dooley, "Hybrid point-and-intensity-based deformable registration for abdominal CT images", Medical Imaging 2005: Image Processing, edited by J. Michael Fitzpatrick, Joseph M. Reinhardt, Proc. of SPIE vol. 5747 (SPIE, Bellingham, WA, 2005), 1605-7422/05, pp. 204-211.

* cited by examiner

TEMPORAL SMOOTHING OF A DEFORMATION MODEL

RELATED APPLICATIONS

This application is related to U.S. application Ser. No. 11/540,327, entitled "Radiation Treatment Planning Using Four-Dimensional Imaging Data," filed on Sep. 28, 2006.

TECHNICAL FIELD

This invention relates to the field of radiation treatment and, in particular, to temporally smoothing a deformation model.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy. In one type of external beam radiation therapy, an external radiation source is used to direct a sequence of X-ray beams at a tumor site from multiple angles, with the patient positioned so the tumor is at the center of rotation (isocenter) of the beam. As the angle of the radiation source changes, every beam passes through the tumor site, but passes through a different area of healthy tissue on its way to the tumor. As a result, the cumulative radiation dose at the tumor is high and the average radiation dose to healthy tissue is low.

The term "radiotherapy" refers to a procedure in which radiation is applied to a target region for therapeutic, rather than necrotic, purposes. The amount of radiation utilized in radiotherapy treatment sessions is typically about an order of magnitude smaller, as compared to the amount used in a radiosurgery session. Radiotherapy is typically characterized by a low dose per treatment (e.g., 100-200 centiGray (cGy)), short treatment times (e.g., 10 to 30 minutes per treatment) and hyperfractionation (e.g., 30 to 45 days of treatment). For convenience, the term "radiation treatment" is used herein to mean radiosurgery and/or radiotherapy unless otherwise noted.

One challenge facing the delivery of radiation to treat pathological anatomies is identifying the target region at a particular point in time because the pathological anatomies may move as a function of the patient's breathing or other natural movements. In radiation treatment, it is useful to accurately locate and track the motion of a target region due to respiratory or other patient motions during the treatment. In order to perform radiation treatment in organs near, for example, the abdomen, lungs, liver, or pancreas, it is useful to take into account the movement of these structures during the patient's respiratory cycle. Conventional methods and systems have been developed for tracking of an internal target region, while measuring and/or compensating for breathing and/or other motions of the patient.

In one conventional method, instead of prescribing a dose solely to the target region, a margin around the target region is defined so that the entire volume traversed by the target region during free breathing receives the prescription dose. Another conventional method controls the amplitude of the patient's respiration, for example, by using a restraint on the chest, so that tissue movement is reduced. A treatment margin is defined, but in this case a smaller treatment volume is used to reflect the reduced amplitude of motion.

Other conventional methods utilize breath holding and respiratory gating to compensate for target region movement during respiration while a patient is receiving conventional radiation treatments. Breath holding is implemented by a patient holding his or her breath at the same point in each breathing cycle, during which time the tumor is treated while it is presumably stationary. A respirometer is often used to measure the tidal volume—the inhaled volume or the change in lung volume during inhalation—and ensure the breath is being held at the same location in the breathing cycle during each irradiation moment. This method takes a relatively long time and often requires training the patient to hold his or her breath in a repeatable manner.

Respiratory gating involves a process of measuring the patient's respiratory cycle during treatment and then turning the radiation beam on only for a predetermined part of the patient's breathing cycle. Respiratory gating does not directly compensate for motions that result from breathing. Rather, radiation treatment is synchronized to the patient's breathing pattern, limiting the radiation beam delivery to times when the tumor is presumably in a reference position. The time taken to treat a patient with respiratory gating is related to the width of the "window" in the breathing cycle during which the beam is enabled. Hence, there is a compromise needed between a wide window (short treatment time, but large amount of target motion during treatment) and a narrow window (small target motion, but long treatment time). Respiratory gating methods also may require the patient to have many sessions of training over several days to breathe in the same manner for long periods of time. Conventional respiratory gating also may expose healthy tissue to radiation before or after the tumor passes into the predetermined position. This can add an additional margin of error of, for example, about 5-10 millimeters (mm) on top of other margins normally used during treatment. However, the prescription volume can usually be smaller than that using free breathing without gating. These conventional methods are limited by the patient's ability to perform breathing functions in a consistent manner over multiple treatment sessions.

Another conventional method of dealing with the motion of a target region during radiation treatment involves the image tracking of fiducial markers that are placed in or near the target region. The position and motion of the fiducial markers is correlated with the position and motion of the target region so that real-time correction of the position of the treatment beam to follow the motion of the target region may be realized, using a real-time continuous imaging method (e.g., fluoroscopy) to continually track the position of the fiducial markers.

Another method of tracking target motion during radiation treatment involves implantation of fiducial markers in or near the target region, as well as the use of non-invasive devices that may be tracked in real time. For example, light emitting diodes (LEDs) may be attached to the skin of the patient's chest and tracked by a camera in the treatment room. The fiducial markers are imaged intermittently, e.g. using X-ray imaging in the treatment room, and a correlation model is built between the positions of the fiducial markers and the positions of the LEDs. Using the real time information on the LED positions, the position of the target is estimated using the correlation model, and the position of the treatment beam is updated accordingly.

Each of these techniques has certain advantages and drawbacks. Without restraint or gating, a fast treatment is possible that is comfortable for the patient. However, some approaches result in the irradiation of a volume of tissue substantially larger than the target region, especially in regions where respiratory motion is large, such as near the diaphragm. Controlling respiratory amplitude can make treatment uncomfortable, and gating causes an increase in treatment time. Performing real-time correction according to the movement of fiducial markers implanted in the target region allows a conformal dose distribution to be delivered quickly. Nevertheless, this method does have a disadvantage that it requires invasive fiducial implantation, and in the case that continuous X-ray imaging is used during treatment, the imaging component itself delivers a substantial dose of radiation to healthy tissue. Real-time correction according to the movement of fiducial markers also may require a radiation delivery device that can be moved quickly and accurately. One such radiation treatment system is the CYBERKNIFE® system developed by Accuray Incorporated, of Sunnyvale, Calif. By mounting a compact X-band linear accelerator on a robot arm assembly, the CYBERKNIFE® radiation treatment system can perform real-time compensation for respiratory motion.

One conventional treatment planning approach using a CYBERKNIFE® radiation treatment system utilizing inverse planning techniques is as follows. First, a target region to be treated and critical structures to be avoided are delineated on a CT scan, or a set of CT slices of a section of the patient's anatomy. More specifically, a three-dimensional (3D) CT scan is composed of a three-dimensional model of section of the patient (e.g., pathological anatomy bearing portion of the body) generated from a collection of two-dimensional (2D) CT slices, with each slice representing a different position in space (for example, a different position along the inferior-superior axis of the patient). In CT scanning, numerous X-ray beams are passed through a section of the body at different angles. Then, sensors measure the amount of radiation absorbed by different tissues. As a patient lies on a couch, an imaging system records X-ray beams from multiple points. A computer program is used to measure the differences in X-ray absorption to form cross-sectional images, or "slices" of the head and brain. These slices are also called tomograms.

Once the target region and critical structures have been delineated, dose constraints may then be applied by a medical physicist to these target regions and critical structures. The medical physicist specifies the minimum dose, and optionally the maximum dose, to the tumor and the maximum dose to other healthy tissues independently. The treatment planning software then selects a set of treatment beam parameters (e.g., direction, total number of beams and duration of each beam) in order to achieve the specified dose constraints. Next, the dose constraints may be altered, tuning structures may be added, and the treatment plan re-optimized until the dose distribution is acceptable. The finalized treatment plan is then sent to a treatment delivery system.

Some conventional treatment planning and delivery systems also implement spatial smoothing functions to represent the deformation of the patient's anatomy during respiration. Spatial smoothing is based on principles of spatial continuity, which is the understanding that adjacent physical points of an object are joined in a continuous manner. As an example, a metal bar exhibits the characteristics of spatial continuity. The many points along a metal bar remain adjacent to one another in a continuous manner as the bar is flexed or bent. In contrast, when the bar is broken, adjacent points move in a non-continuous, or discrete, manner so that they do not remain continuously adjacent to each other. Like a flexed metal bar, physical organs and pathological anatomies are assumed to be spatially continuous. Even though an organ or pathological anatomy may deform over time, the adjacent points of the organ or pathological anatomy are assumed to remain adjacent at all points in time, under normal conditions. Thus, the physical deformations of an organ or pathological anatomy typically conform to the assumptions of spatial continuity. Some conventional radiation treatment systems may implement spatial smoothing functions based on the assumptions of spatial continuity.

Temporal continuity, in contrast to spatial continuity, relates to the movement of a single point over time. In particular, temporal continuity is the understanding that a single point moves along a continuous path of motion over time. In other words, the point does not jump from one location to a non-adjacent location without passing along a continuous path between the two non-adjacent locations. Conventional radiation treatment systems do not use the concept of temporal continuity to model tissue deformation during respiration.

BRIEF DESCRIPTION OF THE DRAWINGS

The present invention is illustrated by way of example, and not by way of limitation, in the figures of the accompanying drawings.

DETAILED DESCRIPTION

The following description sets forth numerous specific details such as examples of specific systems, components, methods, and so forth, in order to provide a good understanding of several embodiments of the present invention. It will be apparent to one skilled in the art, however, that at least some embodiments of the present invention may be practiced without these specific details. In other instances, well-known components or methods are not described in detail or are presented in simple block diagram format in order to avoid unnecessarily obscuring the present invention. Thus, the specific details set forth are merely exemplary. Particular implementations may vary from these exemplary details and still be contemplated to be within the spirit and scope of the present invention.

Embodiments of a method and apparatus are described for approximating a path of movement of a target. In one embodiment, the method includes referencing a temporal sequence of images, identifying a plurality of data points associated with a selected volume element of the volume of interest, and calculating an estimated location of the selected volume element based on a cost function having a constraint which favors continuous spatial motion of the selected volume element over time. Each of the images of the temporal sequence of images depicts a volume of interest. Each of the plurality of data points corresponds to one of the images. Other embodiments of the method and apparatus are also described.

Figure 1:
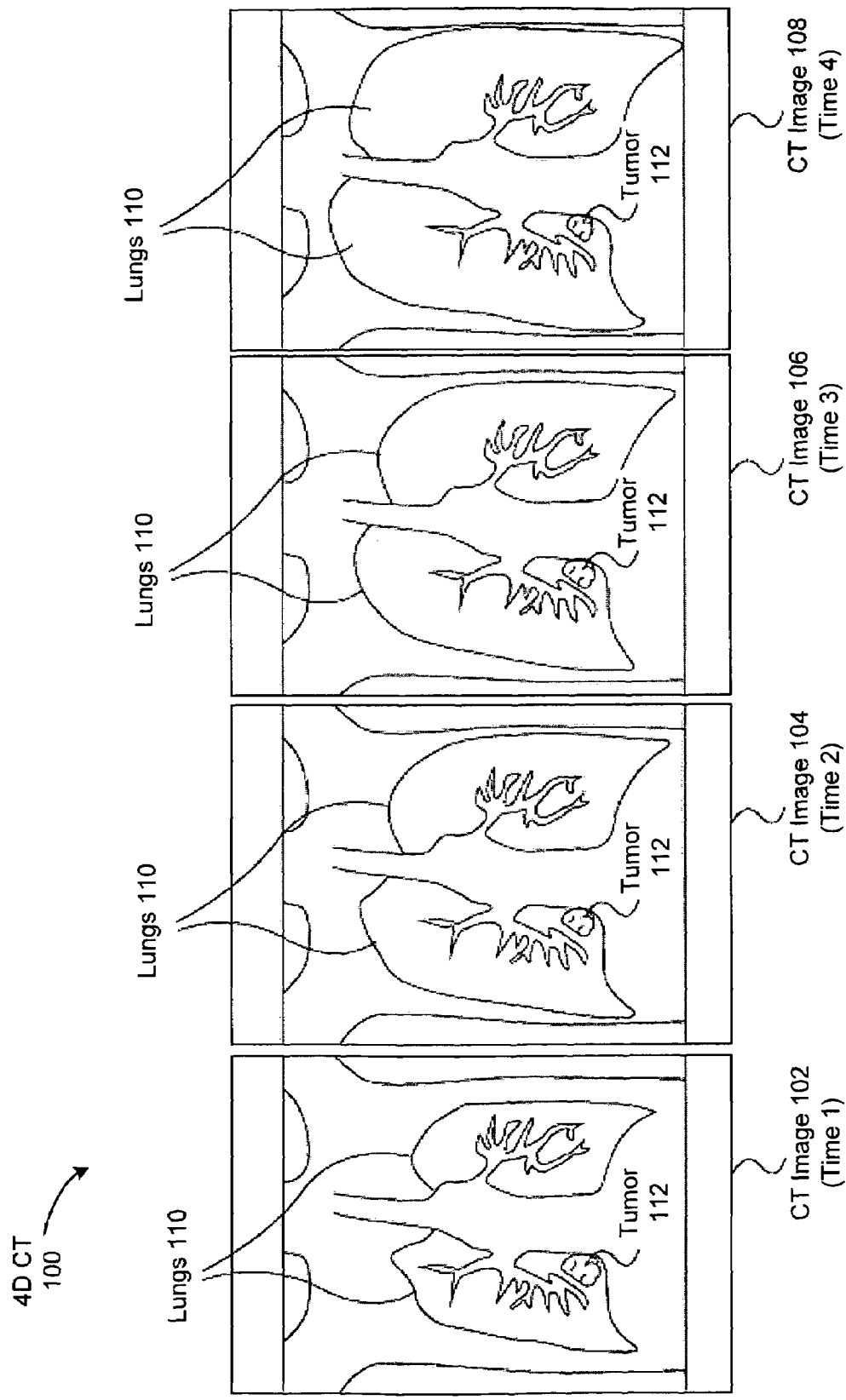
FIG. 1 illustrates one embodiment of a four-dimensional (4D) computed tomography (CT) scan.

FIG. 1 illustrates one embodiment of a four-dimensional (4D) computed tomography (CT) scan 100. In general, the 4D CT scan 100 conveys four dimensions of information for the content of the scan 100. In one embodiment, the four dimensions include three spatial dimensions and one temporal dimension. In particular, the 4D CT scan 100 includes a collection of three dimensional (3D) spatial images taken at different points in time in a motion cycle (e.g., during the respiratory cycle, cardiac cycle, artery pulsation, etc. of a patient) with a known temporal relationship.

The conceptual illustration of FIG. 1 depicts a tumor 112 in a patient's chest region. The tumor 112 moves over time, as shown in the corresponding CT images 102, 104, 106, and 108. Each of the CT images 102, 104, 106, and 108 are taken at a particular point in time (i.e., time 1, time 2, time 3, and time 4, respectively) of the respiratory cycle. The CT images 102, 104, 106, and 108 also show the relationship between the tumor 112 and the lungs 110 at each point in time.

In another embodiment, an amplitude index is associated with the respiratory cycle in each of the CT images 102, 104, 106, and 108. For example, amplitude 1 may be associated with the minimum height reached by the chest wall of the patient, and amplitude 4 may be associated with the maximum chest wall height. The intermediate amplitudes 2 and 3 may be associated with intermediate positions of the chest wall.

In one embodiment, a time index is associated with the respiratory cycle so that each of the CT images 102, 104, 106, and 108 is associated with a subset of the respiratory cycle. For example, time 1 may be associated with a full expiration by the patient, and time 4 may be associated with a full inspiration by the patient. The intermediate times 2 and 3 may be associated with intermediate points in the respiratory cycle. In one embodiment, the series of CT images 102, 104, 106, and 108 depict displacement and deformation of the tumor 112 over time.

In one embodiment, the 4D CT scan 100 may be generated using a 4D CT scanner such as, for example, a 4D CT scanner produced by General Electric Corporation. Alternatively, other 4D CT scanners may be used. Some 4D CT scanners include a device such as a spirometer, strain gauge, or optical tracker, that is configured to take instantaneous measurements of the patient's position in the respiratory cycle. When a slice is acquired, the current respiratory measurement position is recorded. In one embodiment, this measurement is used to place the CT slice in one of the 3D CT images 102, 104, 106, or 108 with the index closest to the given measurement of the respiratory cycle. In contrast to conventional 3D CT scans, in which some subsets of slices may be acquired simultaneously, the timing of the slice acquisition in conventional 3D CT scanning is not typically indexed to physical processes such as a respiratory cycle, other than to optionally halt the breathing cycle by instructing the patient to cease breathing while the scan is taken.

The 4D CT scan 100 data may be acquired in a single motion cycle, or may be acquired over multiple motion cycles. In some embodiments, two or more conventional 3D CT images may be acquired during breath hold at different points in the breathing cycle (e.g., at full inspiration and full expiration). Accordingly, the term "4D CT scan" is used herein to mean a set of two or more 3D images that represent different time points in a motion cycle regardless of the method of acquiring the scan data.

In some embodiments, the 4D CT scan 100 is used to develop a radiation treatment plan. The 4D CT scan 100 may include data of the motion of a target region and surrounding structures. For example, the data may describe translation, rotation, and deformation of the target region and surrounding structures. A treatment planning system may use this data to develop a treatment plan using the data from the 4D CT scan 100. In one embodiment, the data from the 4D CT scan 100 is imported into a treatment planning system. Alternatively, the data from the 4D CT scan 100 may already reside on a diagnostic CT imaging system that is also used for the treatment planning system that is used to perform the diagnostic 4D CT imaging. Some embodiments of the treatment planning system may be fully compliant with DICOM standards for the distribution and viewing of medical images and the DICOM-RT standard for viewing radiotherapy information overlaid on medical images.

In order to develop a radiation treatment plan, the treatment planning system may delineate a target on a CT image. Delineation of a target is described in more detail with reference to FIG. 2. In one embodiment, one of the 4D CT images 102, 104, 106, or 108 may be used for delineation of the target as well as critical structures. Alternatively, delineation may be performed using a standard CT image acquired using conventional techniques such as breath holding (i.e., a patient holding their breath). In another embodiment, delineation may be performed on an image of a different modality. For example, conventional magnetic resonance imaging (MRI) may be used for delineation.

The treatment planning system also may define a motion (e.g., deformation) model to describe the movement of the target and surrounding structures within the treatment region. The output of this model is a "deformation field" (i.e., a representation of the movement of any spatial position within the imaging volume). The model may be defined, for example, using non-rigid registration techniques. Non-rigid registration techniques are well known in the art; accordingly, a more detailed discussion is not provided. Additional techniques may be used to define the motion model, as described below with reference to FIGS. 3 and 4.

The treatment planning software also may calculate a dose distribution using the motion model. When the dose distribution is calculated, the motion model together with a weighting, according to the relative amount of time spent at each point, or node, in the motion cycle, is applied to give a dose estimate at each spatial position. This dose information may be represented either as a single distribution, using the motion model to refer the dose information into the space of the image used for delineation, or as a set of dose distributions, each one in the space of one of the 3D images making up the 4D CT. In this way, the treatment plan takes dose distribution and motion (e.g., due to respiration) into account, and a view of the resulting treatment dose may be obtained. The treating physician or physicist may then use this dose information to change the treatment margins and/or re-optimize the treatment plan. The treatment plan also may be reviewed after optimization to view effects of the target motion on the dose distribution.

Figure 2:
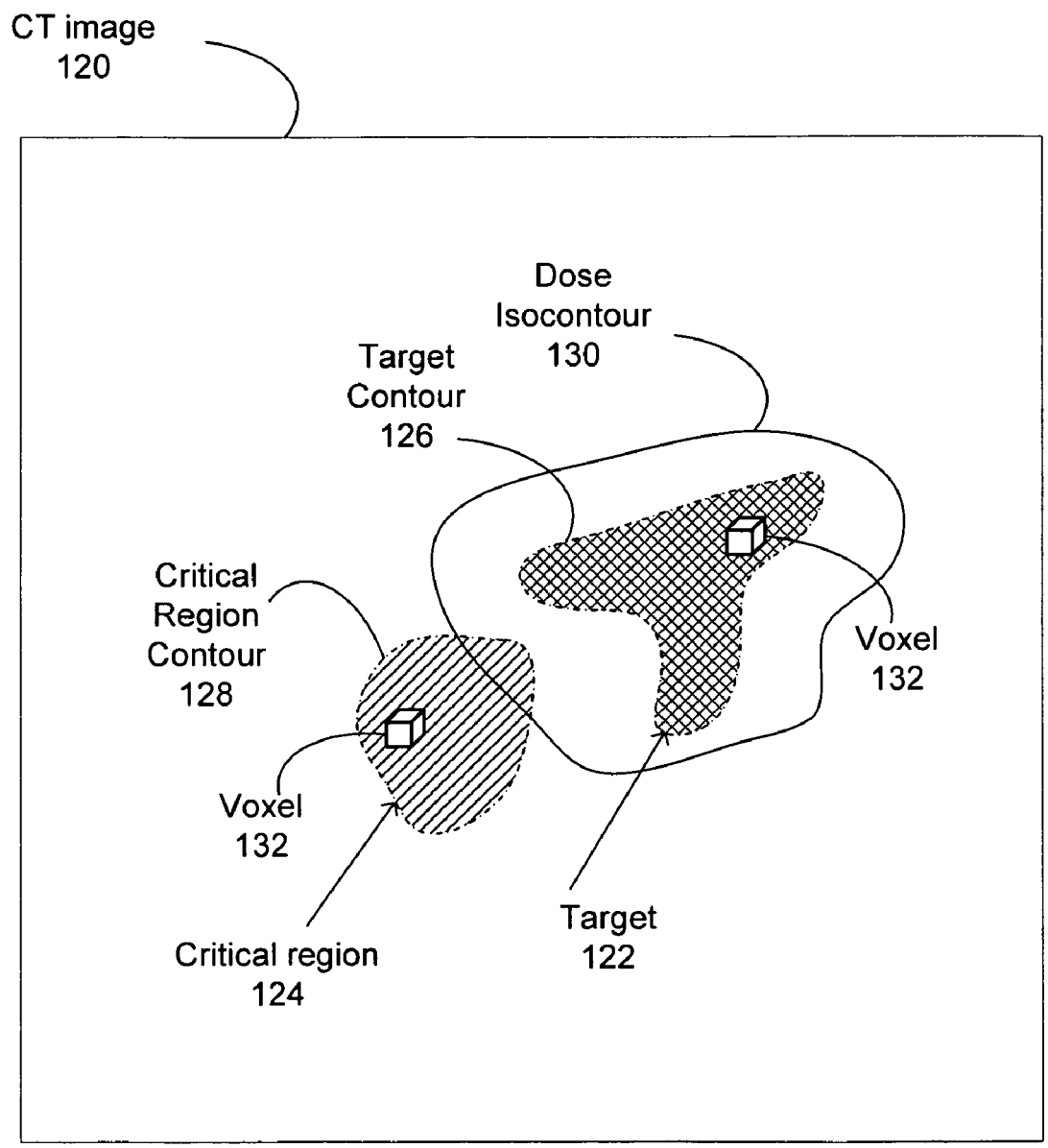
FIG. 2 illustrates one embodiment of a graphical output of a treatment planning system displaying a slice of a CT image.

FIG. 2 illustrates one embodiment of a graphical output of a treatment planning system displaying a slice of a CT image 120. In one embodiment, the CT image 120 may be used to delineate a target 122 (e.g., pathological anatomy such as a tumor, lesion, vascular malformation, etc.) and a critical region 124. The target 122 is targeted for treatment, and the critical region 124 may be identified to limit the amount of radiation applied to the critical region 124. In one embodiment, the target 122 and critical region 124 include multiple volume elements, or voxels, 132. A volume element, or voxel, is a volume of space within a volume of interest (VOI) such as a target 122. In one embodiment, a voxel represents a volume having dimensions of approximately 0.5 by 0.5 by 1.25 millimeters, although other sizes of voxels may be used.

The treatment planning software enables the generation of a target contour 126 around the target 122 and a critical region contour 128 around the critical region 124. In one embodiment, a user manually delineates points on a display. The points are then used by the treatment planning software to generate the corresponding contours. Alternatively, the delineation process may be automated. Based on a specified minimum dose to the target 122 and a specified maximum dose to the critical region 124, the treatment planning software generates the dose isocontour 130 for the target 122. The dose isocontour 130 represents a given dose percentage (e.g., 60%, 70%, 80%, etc.) of a specified prescription dose for the target 122. Ideally, the dose isocontour 130 should perfectly match the contour of the target 122. However, in some cases, the dose isocontour 130 generated by the treatment planning software is not optimal, and may include portions of the critical region 124, as illustrated in FIG. 2.

Two of the principal measurements for an effective radiation treatment are homogeneity and conformality. Homogeneity is the uniformity of the radiation dose over the volume of the target and may be characterized by a dose volume histogram (DVH). A typical graph of the DVH shows, on a horizontal axis, dose values, either absolute or as a percentage of a given dose, e.g., maximum dose or prescription dose. On the vertical axis, a typical DVH shows either the percentage or absolute volume of the structure (target or critical region) receiving at least the given dose. An ideal DVH for the target 122 would be a rectangular function in which the dose is 100% of the prescribed dose over the volume of the target 122. A desirable DVH for a critical region 124 would have a function profile in which the volume of the critical structure(s) 124 receives as little of the prescribed dose as possible.

Conformality is the degree to which the radiation dose matches (conforms to) the shape and extent of the target 122 (e.g., tumor) in order to avoid damage to adjacent critical structures 124. More specifically, conformality with respect to a target 122 is a measure of the amount of the region receiving the prescription (Rx) dose or more, that is contained within the target. Conformality may be measured using a conformality index (CI)=(total volume at >=Rx dose)/(target volume at >=Rx dose). Perfect conformality results in a CI=1. With conventional radiation treatment, using treatment planning software, a clinician identifies a dose isocontour for a corresponding target 122 for application of a treatment dose (e.g., 3000 cGy).

Figure 3:
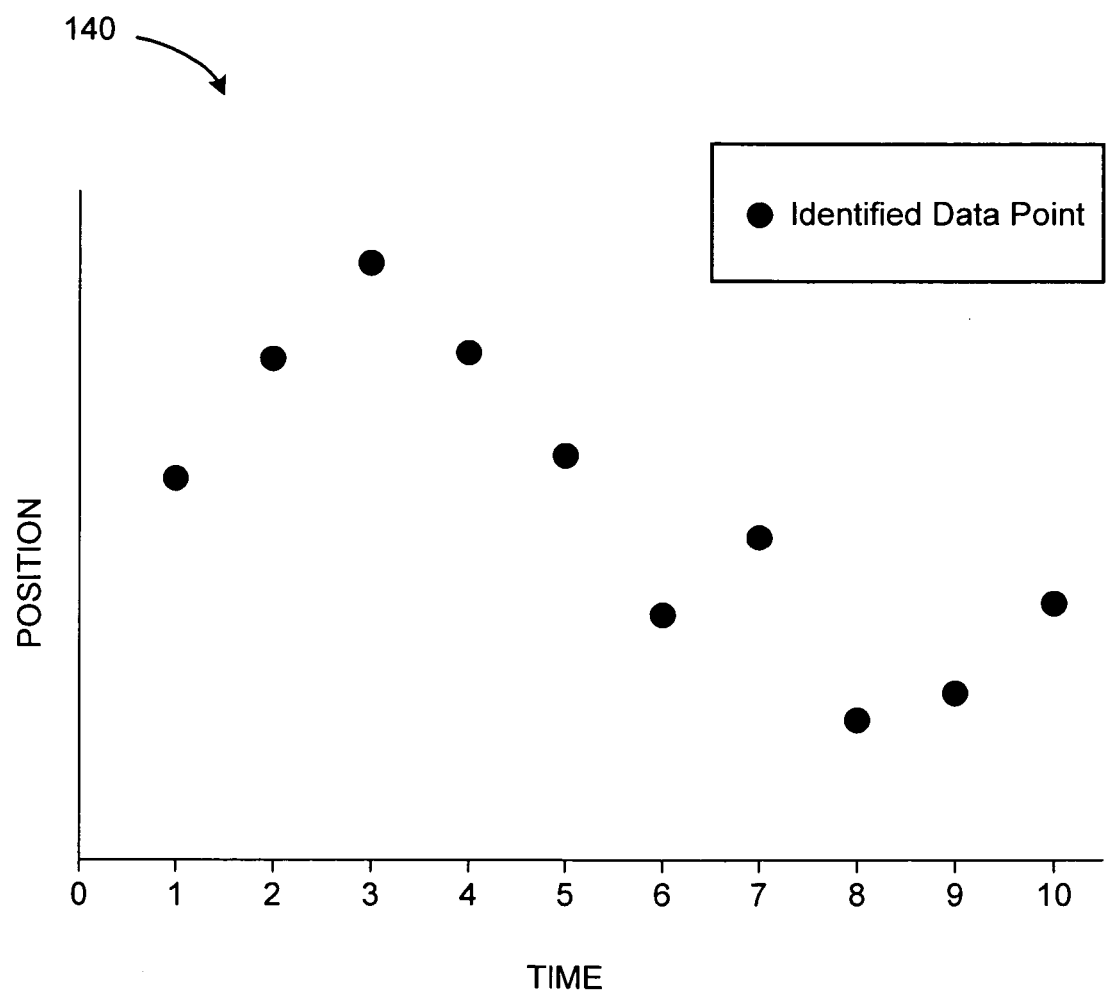
FIG. 3 illustrates a graph of one embodiment of a plurality of target positions over time.

FIG. 3 illustrates a graph 140 of one embodiment of a plurality of target positions over time. Each target position is represented by an identified data point on the graph 140. For example, the identified data point at time 5 may correspond to the position of the target 122 in the CT image indexed at time 5. In one embodiment, the target positions represented by the identified data points are referenced to a known target position or another known reference point. Although the graph 140 shows a single position axis corresponding to a single direction of movement (e.g., up and down), similar graphs 140 may be constructed to depict movement of the target 122 in other directions (e.g., side-to-side) as well.

In some embodiments, the position of each volume element, or voxel, 132 within the target 122 is identified and indicated on a graph similar to the graph 140 of FIG. 3. Thus, the graph 140 of FIG. 2 may show the position and movement, depicted by the identified data points, of a single voxel 132 over time. In one embodiment, the positions of a specific voxel 132 are identified from a motion model, or deformation model, as described below.

Figure 4:
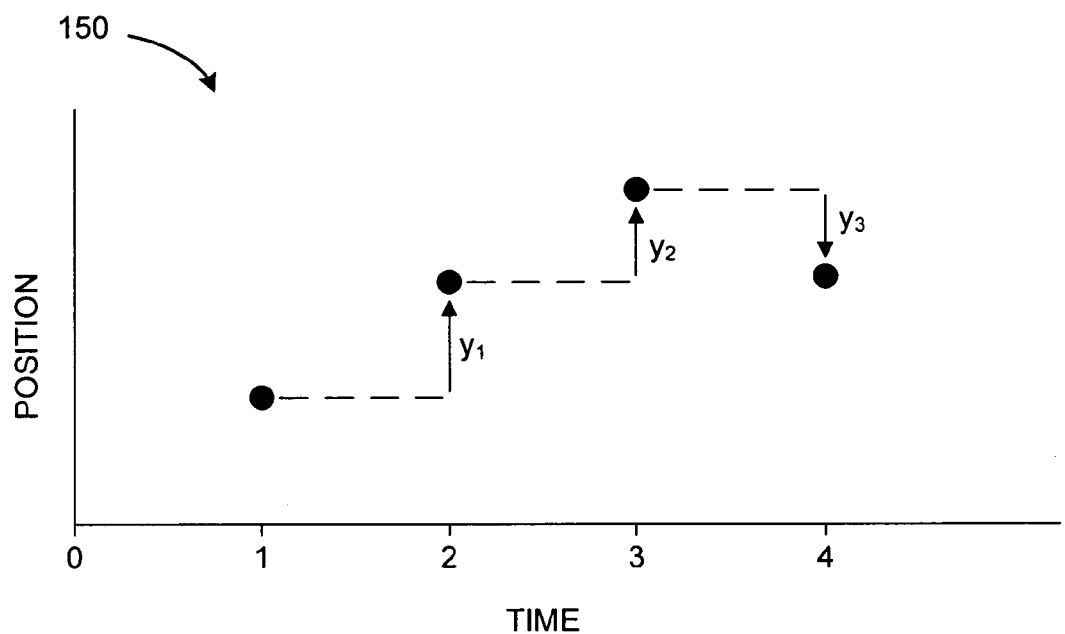
FIG. 4 illustrates a graph of one embodiment of an incremental deformation model.

FIG. 4 illustrates a graph 150 of one embodiment of an incremental deformation model. In general, the incremental deformation model as applied to the voxel 132 is described by determining the incremental movement of the voxel 132 from one identified data point to the next identified data point. In the depicted embodiment, the deformation model identifies the location of the voxel 132 at time 1, and then identifies the location of the voxel 132 at time 2 using an offset, $y_1$, from the location corresponding to the identified data point at time 1. Similarly, the location of the voxel 132 at time 3 is defined using an offset, $y_2$, from the location corresponding to the identified data point at time 2. In other words, the location of the voxel 132 at each point in time is defined by the one or more offsets from the identified data point corresponding to the previous location of the voxel 132. Although only one offset is used in the graph 150 of FIG. 4, other embodiments may use more offsets corresponding to more spatial dimensions (e.g., an x-offset or a z-offset).

Figure 5:
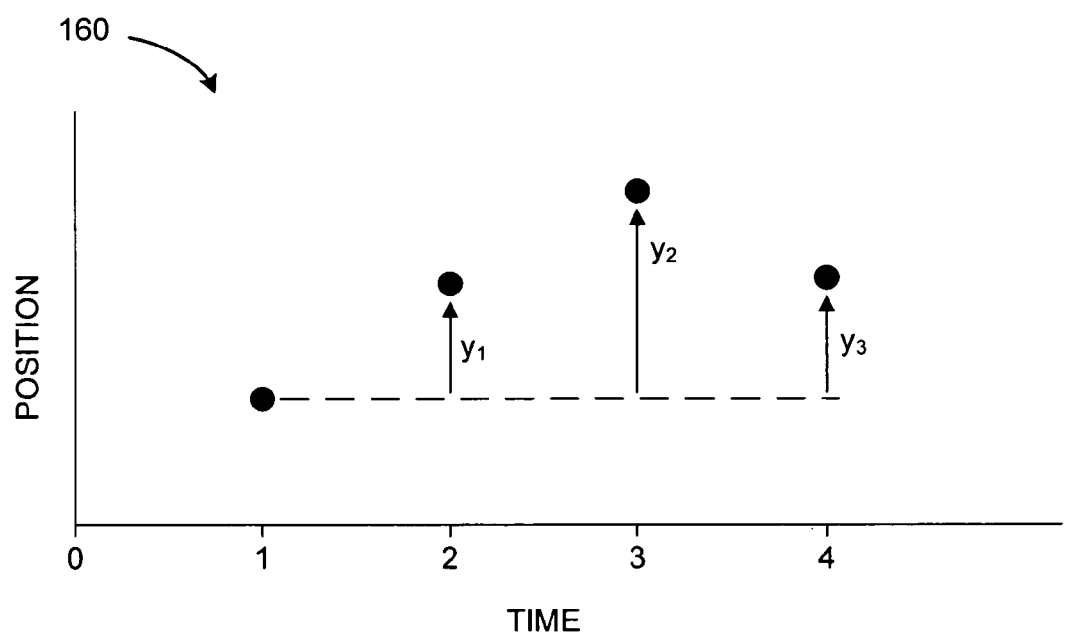
FIG. 5 illustrates a graph of one embodiment of a cumulative deformation model.

FIG. 5 illustrates a graph 160 of one embodiment of a cumulative deformation model. In contrast to the incremental deformation model of FIG. 4, the cumulative deformation model of FIG. 5 as applied to the voxel 132 determines the cumulative movement of the voxel 132 from a single reference location. As an example, the location of the voxel 132 at time 1 is used as a reference in the graph 160 of FIG. 5. In the depicted embodiment, the deformation model identifies the location of the voxel 132 at time 2 using an offset, $y_1$, from the location corresponding to the identified data point at time 1. Then, the deformation model identifies the location of the voxel 132 at time 3 using another offset, $y_2$, from the location corresponding to the identified data point at time 1. In other words, the location of the voxel 132 at each point in time is defined by one or more offsets from the identified data point corresponding to the reference location of the voxel 132 (e.g., at time 1). As described above, other embodiments may use more offsets corresponding to other spatial dimensions.

Figure 6:
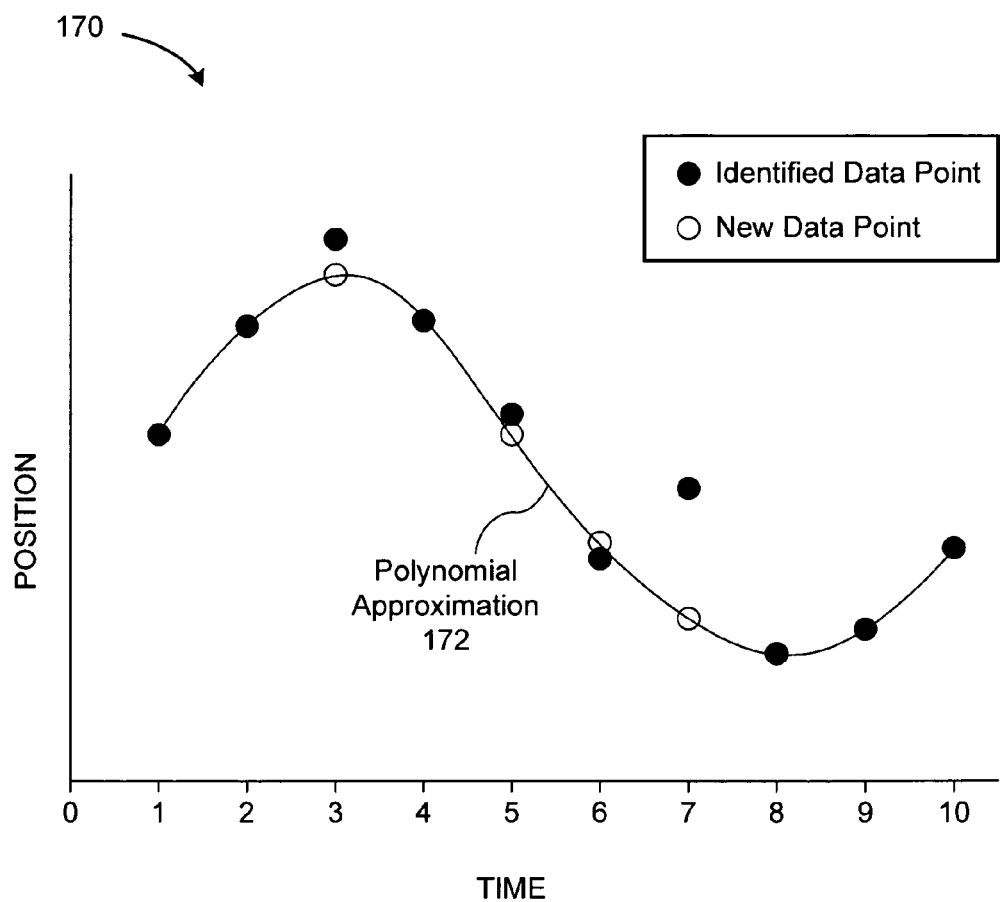
FIG. 6 illustrates a graph of one embodiment of a polynomial approximation of the target positions over time.

FIG. 6 illustrates a graph 170 of one embodiment of a polynomial approximation 172 of the target positions over time. The polynomial approximation 172 may be any order of polynomial, depending on the type of motion that the polynomial approximation 172 represents. For example, a first order polynomial may be used to approximate a linear movement. Other orders of polynomials may be used to represent other types of movements. In some embodiments, other types of approximations may be used to approximate the movement of the voxel 132 in one or more dimensions. For example, B-spline interpolation may be used to approximate the movement of a voxel 132.

Once the polynomial approximation 172 is generated, new data points may be defined and used to modify or replace identified data points that are inconsistent with the polynomial approximation 172. In this way, some of the identified data points may be disregarded if they are inconsistent with the polynomial approximation 172 and, hence, inconsistent with an assumption that each voxel 132 moves in a continuous path among several identified data points.

Figure 7:
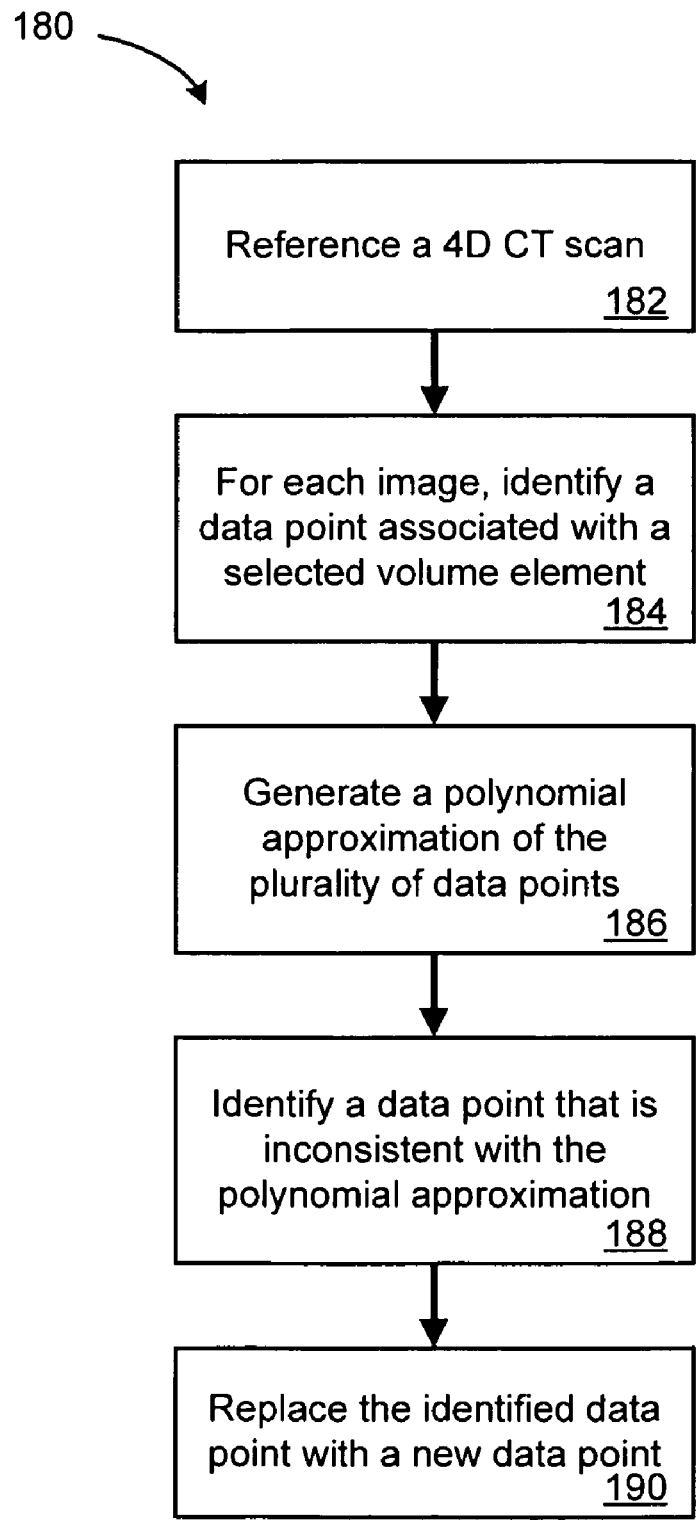
FIG. 7 illustrates a flow chart diagram of a replacement method for replacing an identified data point with a new data point.

FIG. 7 illustrates a flow chart diagram of a replacement method 180 for replacing an identified data point with a new data point. In one embodiment, the treatment planning system references 182 a 4D CT scan 100. For each CT image 102, 104, 106, and 108 of the 4D CT scan 100, the treatment planning system identifies 184 a data point associated with a selected voxel 132. The treatment planning system then generates 186 a polynomial approximation 172 of the identified data points and identifies 188 any data points which are inconsistent with the polynomial approximation 172. The treatment planning system then replaces 190 the inconsistent identified data points with new data points which are consistent with the polynomial approximation 172. The depicted replacement method 180 then ends.

Figure 8:
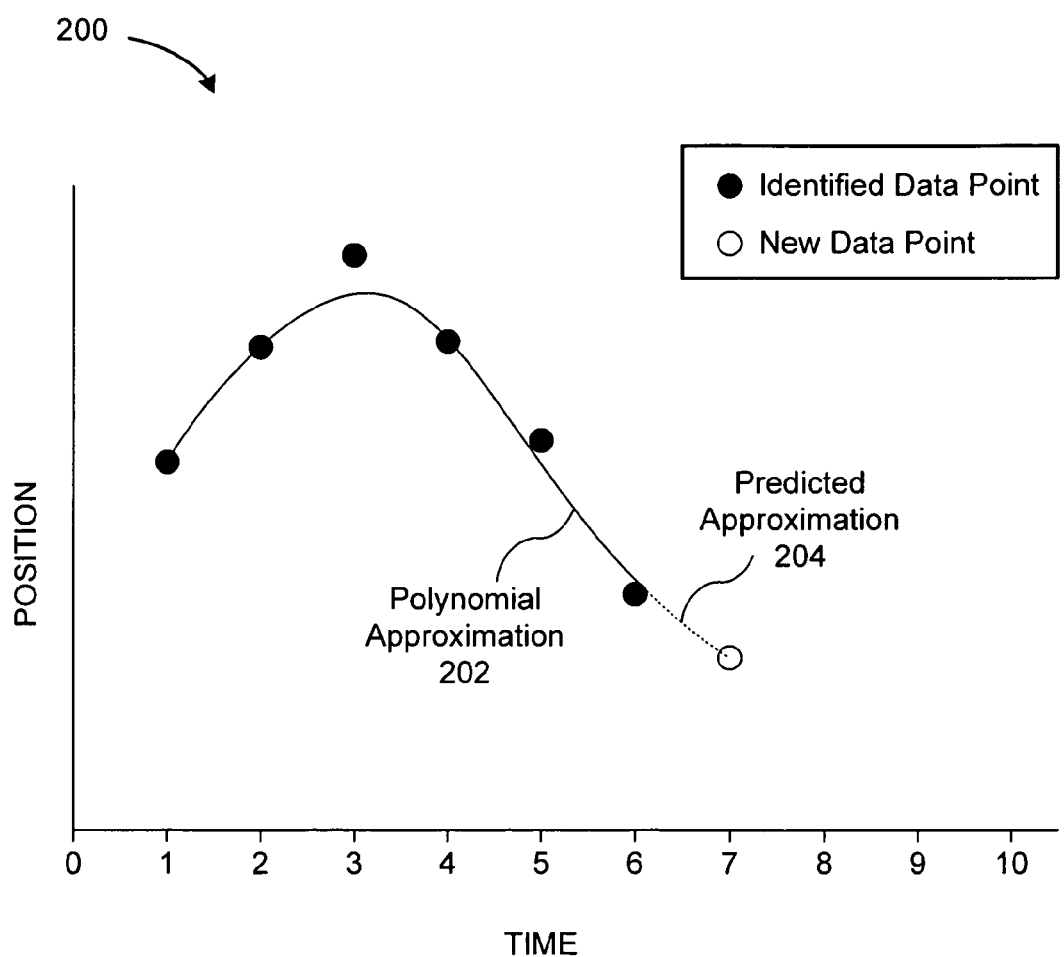
FIG. 8 illustrates a graph of another embodiment of a polynomial approximation of the target positions over time.

FIG. 8 illustrates a graph 200 of another embodiment of a polynomial approximation 202 of the target positions over time. Once the polynomial approximation 202 is generated, a new data point may be defined and used to predict the next location of the selected voxel 132 at a location that is consistent with the polynomial approximation 202. In one embodiment, the polynomial approximation 202 may include a predicted approximation 204 that extends beyond the last identified data point. In this way, the locations of future identified data points may be anticipated using the polynomial approximation 202 based on the assumption that each voxel 132 moves in a continuous path among several identified data points.

Figure 9:
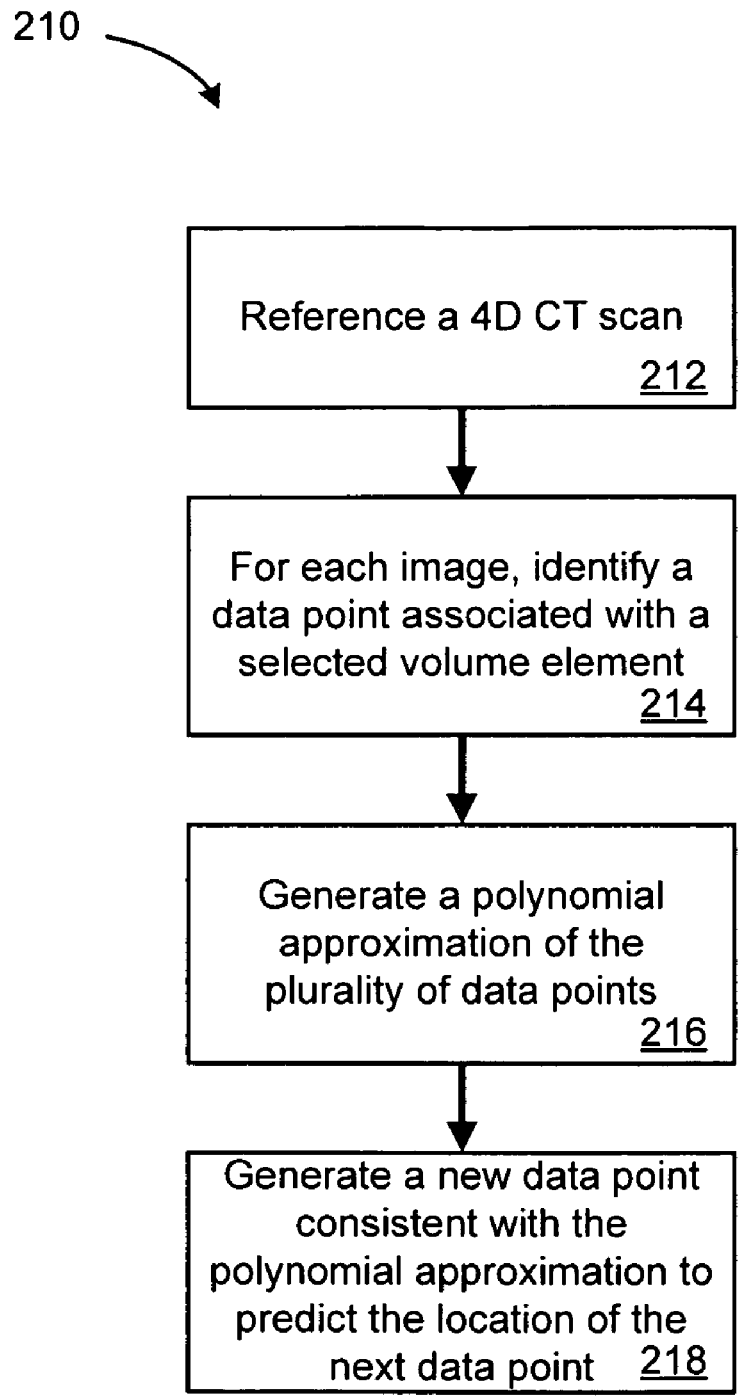
FIG. 9 illustrates a flow chart diagram of a prediction method for predicting a location of a new data point based on the polynomial approximation of the identified data points.

FIG. 9 illustrates a flow chart diagram of a prediction method 210 for predicting a location of a new data point based on the polynomial approximation 202 of the identified data points. In one embodiment, the treatment delivery system references 212 a 4D CT scan 100. For each CT image 102, 104, 106, and 108 of the 4D CT scan 100, the treatment delivery system identifies 214 a data point associated with a selected voxel 132. The treatment delivery system then generates 216 a polynomial approximation 202 of the identified data points. Using the polynomial approximation 202, the treatment delivery system generates a new data point corresponding to a location which is consistent with the prediction approximation 204 of the polynomial approximation 202. The depicted prediction method 210 then ends.

In one embodiment, the polynomial approximation 202 is used while the deformation model is being computed. That is, while the deformations mapping the position of the voxel 132 between the data points are being calculated, for example, using an iterative optimization method, one of the constraints in an optimization cost function is that the polynomial approximation 202 relating the respective positions of the voxel 132 with respect to each of the data points must be obeyed, either exactly or approximately.

When trying to compute a deformation field that maps one image (the floating image) to another (the reference image), the cost function takes the floating image and the current state of the deformation field, and outputs a value that is some measure of how well the deformation field applied to the floating image gives an image that matches the reference. An example cost function would be the sum of squared difference in CT number between the reference image and the floating image after the current deformation field is applied. In one embodiment, the cost function includes a constraint such as a time derivative of motion of at least some of the plurality of identified data points.

In some embodiments, the cost function implements a smoothing function which uses one set of data as input and generates a modified set of data, which is constrained to remain continuous as one or more of the parameters change, as output. For example, a temporal smoothing function may use time as the parameter over which the data is constrained to be continuous. In order to implement a temporal smoothing function, an algorithm may be applied to a set of data, each representing a different point in time, so that the output of the algorithm is a new set of data, constrained so that the data appears to be a continuous function of time. In a particular embodiment, the input data is a deformation model with parameters x, y, z, and t, and the output of the algorithm is a deformation model which appears to be continuous in the time parameter, t, but not necessarily in the spatial parameters x, y, and z. In some embodiments, the cost function constraint is a time derivative of motion of at least some of the plurality of identified data points.

In another embodiment, the polynomial approximation 202 is used after the deformation model has been computed. That is, the deformations mapping the position of the voxel 132 between the data points are calculated, for example, using an iterative optimization method, but without any temporal smoothness constraint such as that given by the polynomial approximation 202. After the optimization process has finished, the deformation model is refined, i.e., the values of the deformation offsets are changed, so that they better obey the polynomial approximation 202.

Figure 10:
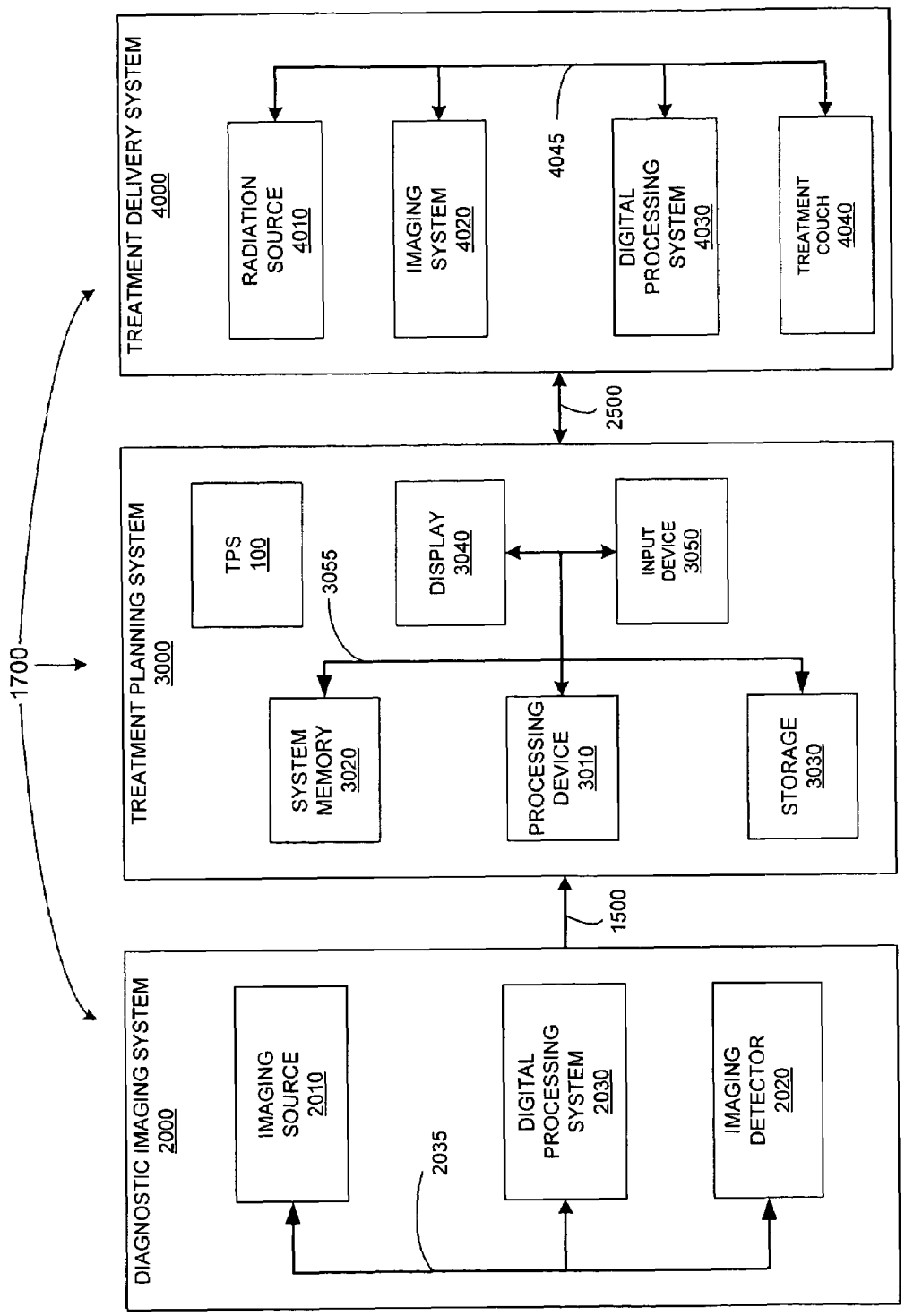
FIG. 10 illustrates one embodiment of a treatment system which may be used to perform radiation treatment.

FIG. 10 illustrates one embodiment of a treatment system 1700 which may be used to perform radiation treatment. The depicted treatment system 1700 includes a diagnostic imaging system 2000, a treatment planning system 3000, and a treatment delivery system 4000.

Diagnostic imaging system 2000 is representative of a system capable of producing medical diagnostic images of a VOI that may be used for subsequent diagnosis, treatment planning and/or treatment delivery. For example, diagnostic imaging system 2000 may be a computed tomography (CT) system, a magnetic resonance imaging (MRI) system, a positron emission tomography (PET) system, an ultrasound system or the like. For ease of discussion, diagnostic imaging system 2000 is discussed at times in relation to a CT X-ray imaging modality. However, other imaging modalities such as those above may also be used.

Diagnostic imaging system 2000 includes an imaging source 2010 to generate an imaging beam (e.g., X-rays, ultrasonic waves, radio frequency waves, etc.) and an imaging detector 2020 to detect and receive the beam generated by imaging source 2010, or a secondary beam or emission stimulated by the beam from the imaging source (e.g., in an MRI or PET scan). In one embodiment, imaging system 2000 represents a 4D CT scanner as discussed above. In one embodiment, diagnostic imaging system 2000 may include two or more diagnostic X-ray sources and two or more corresponding imaging detectors. For example, two X-ray sources may be disposed around a patient to be imaged, fixed at an angular separation from each other (e.g., 90 degrees, 45 degrees, etc.) and aimed through the patient toward (an) imaging detector(s) which may be diametrically opposed to the X-ray sources. A single large imaging detector, or multiple imaging detectors, may also be used that would be illuminated by each X-ray imaging source. Alternatively, other numbers and configurations of imaging sources and imaging detectors may be used.

The imaging source 2010 and the imaging detector 2020 are coupled to a digital processing system 2030 to control the imaging operation and process image data. Diagnostic imaging system 2000 includes a bus or other means 2035 for transferring data and commands among digital processing system 2030, imaging source 2010 and imaging detector 2020. Digital processing system 2030 may include one or more general-purpose processors (e.g., a microprocessor), special purpose processor such as a digital signal processor (DSP) or other type of device such as a controller or field programmable gate array (FPGA). Digital processing system 2030 may also include other components (not shown) such as memory, storage devices, network adapters and the like. Digital processing system 2030 may be configured to generate digital diagnostic images in a standard format, such as the DICOM (Digital Imaging and Communications in Medicine) format, for example. In other embodiments, digital processing system 2030 may generate other standard or non-standard digital image formats. Digital processing system 2030 may transmit diagnostic image files (e.g., the aforementioned DICOM formatted files) to treatment planning system 3000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 3000 includes a processing device 3010 to receive and process image data such as the 4D CT data discussed above. Processing device 3010 may represent one or more general-purpose processors (e.g., a microprocessor), special purpose processor such as a digital signal processor (DSP) or other type of device such as a controller or field programmable gate array (FPGA). Processing device 3010 may be configured to execute instructions for performing the operations of the methods discussed herein that, for example, may be loaded in processing device 3010 from storage 3030 and/or system memory 3020.

Treatment planning system 3000 may also include system memory 3020 that may include a random access memory (RAM), or other dynamic storage devices, coupled to processing device 3010 by bus 3055, for storing information and instructions to be executed by processing device 3010. System memory 3020 also may be used for storing temporary variables or other intermediate information during execution of instructions by processing device 3010. System memory 3020 may also include a read only memory (ROM) and/or other static storage device coupled to bus 3055 for storing static information and instructions for processing device 3010.

Treatment planning system 3000 may also include storage device 3030, representing one or more storage devices (e.g., a magnetic disk drive or optical disk drive) coupled to bus 3055 for storing information and data, for example, the 4D CT data discussed above. Storage device 3030 may also be used for storing instructions for performing the treatment planning methods discussed herein.

Processing device 3010 may also be coupled to a display device 3040, such as a cathode ray tube (CRT) or liquid crystal display (LCD), for displaying information (e.g., a two-dimensional or three-dimensional representation of the VOI) to the user. An input device 3050, such as a keyboard, may be coupled to processing device 3010 for communicating information and/or command selections to processing device 3010. One or more other user input devices (e.g., a mouse, a trackball or cursor direction keys) may also be used to communicate directional information, to select commands for processing device 3010 and to control cursor movements on display 3040.

It will be appreciated that treatment planning system 3000 represents only one example of a treatment planning system, which may have many different configurations and architectures, which may include more components or fewer components than treatment planning system 3000 and which may be employed with the present invention. For example, some systems often have multiple buses, such as a peripheral bus, a dedicated cache bus, etc. The treatment planning system 3000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 3000 may share its database (e.g., data stored in storage device 3030) with a treatment delivery system, such as treatment delivery system 4000, so that it may not be necessary to export from the treatment planning system prior to treatment delivery. Treatment planning system 3000 may be linked to treatment delivery system 4000 via a data link 2500, which may be a direct link, a LAN link or a WAN link as discussed above with respect to data link 1500. It should be noted that when data links 1500 and 2500 are implemented as LAN or WAN connections, any of diagnostic imaging system 2000, treatment planning system 3000 and/or treatment delivery system 4000 may be in decentralized locations such that the systems may be physically remote from each other. Alternatively, any of diagnostic imaging system 2000, treatment planning system 3000 and/or treatment delivery system 4000 may be integrated with each other in one or more systems.

Treatment delivery system 4000 includes a therapeutic and/or surgical radiation source 4010 to administer a prescribed radiation dose to a target volume in conformance with a treatment plan. Treatment delivery system 4000 may also include an imaging system 4020 to capture intra-treatment images of a patient volume (including the target volume) for registration or correlation with the diagnostic images described above in order to position the patient with respect to the radiation source. Treatment delivery system 4000 may also include a digital processing system 4030 to control radiation source 4010, imaging system 4020, and a patient support device such as a treatment couch 4040. Digital processing system 4030 may include one or more general-purpose processors (e.g., a microprocessor), special purpose processor such as a digital signal processor (DSP) or other type of device such as a controller or field programmable gate array (FPGA). Digital processing system 4030 may also include other components (not shown) such as memory, storage devices, network adapters and the like. Digital processing system 4030 may be coupled to radiation source 4010, imaging system 4020 and treatment couch 4040 by a bus 4045 or other type of control and communication interface.

It should be noted that the described treatment system 1700 is only representative of an exemplary system. Other embodiments of the system 1700 may have many different configurations and architectures and may include fewer or more components.

Figure 11:
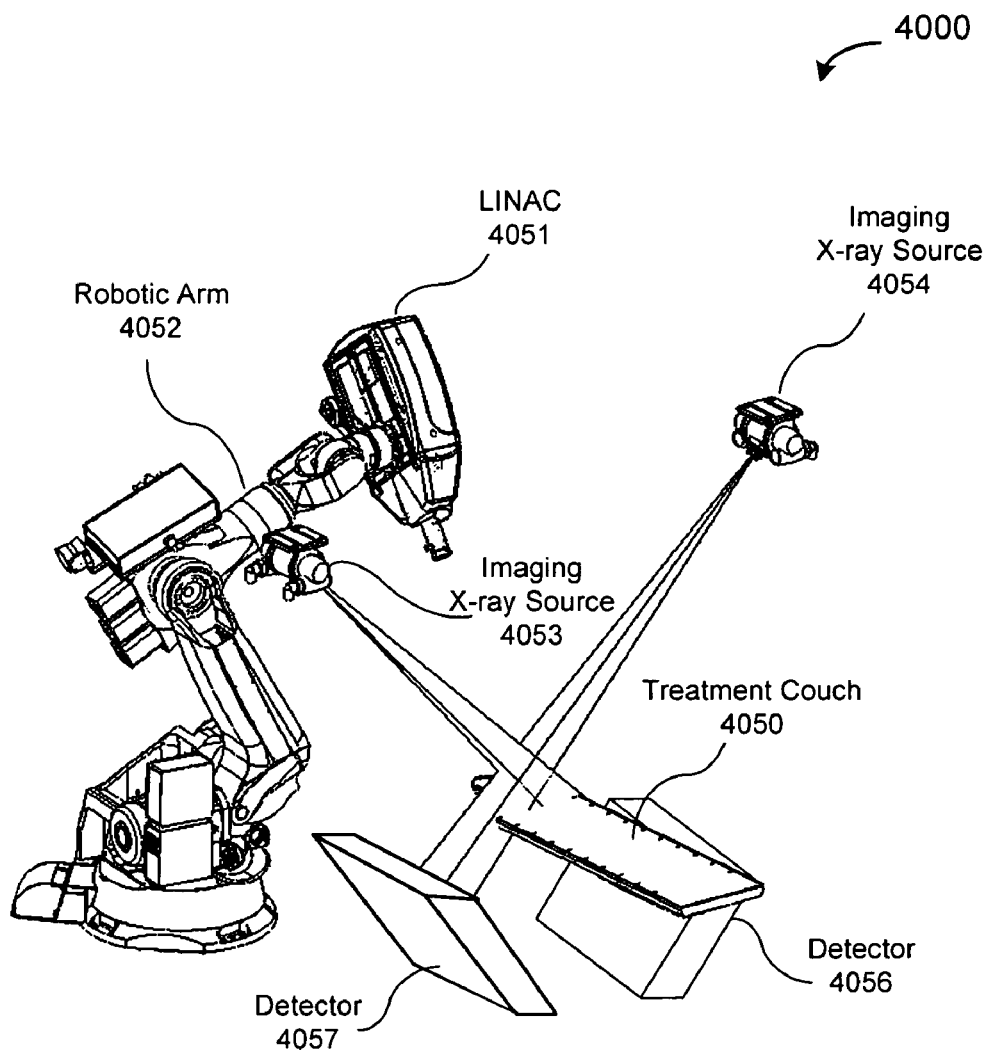
FIG. 11 illustrates one embodiment of a robotic, image-guided radiation treatment system.
Figure 12:
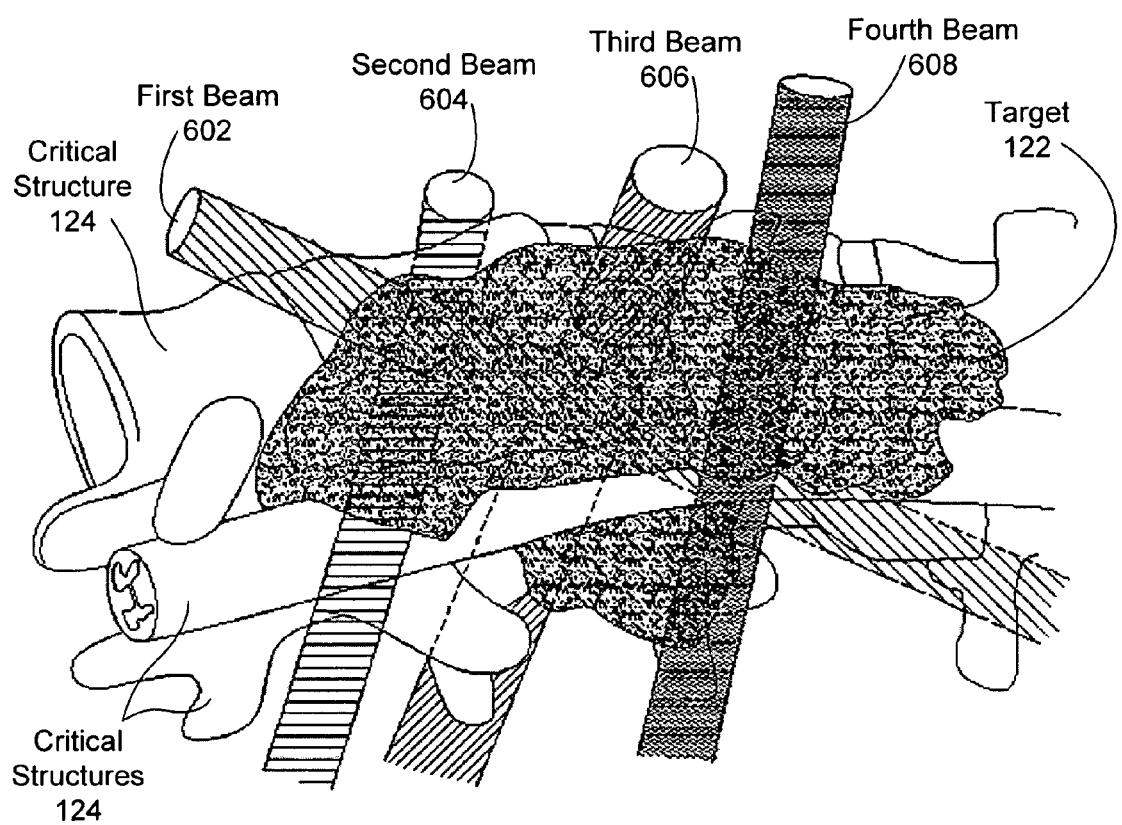
FIG. 12 illustrates a three-dimensional perspective view of one embodiment of a non-isocentric beam delivery process.

FIG. 11 illustrates one embodiment of a robotic, image-guided radiation treatment system 4000. One example of such a system 4000 is the CYBERKNIFE® system developed by Accuray Incorporated, of Sunnyvale, Calif. In FIG. 11, radiation source 4010 may be represented by a linear accelerator (LINAC) 4051 mounted on the end of a robotic arm 4052 having multiple (e.g., 5 or more) degrees of freedom in order to position the LINAC 4051 to irradiate a pathological anatomy (target or volume) with beams delivered from many angles in an operating volume (e.g., a sphere) around the patient. Treatment may involve beam paths with a single isocenter (point of convergence), multiple isocenters, or with a non-isocentric approach (i.e., the beams need only intersect with the pathological target volume and do not necessarily converge on a single point, or isocenter, within the target as illustrated in FIG. 12). Treatment can be delivered in either a single session (mono-fraction) or in a small number of sessions as determined during treatment planning. With treatment delivery system 4000, in one embodiment, radiation beams may be delivered according to the treatment plan without fixing the patient to a rigid, external frame to register the intra-operative position of the target volume with the position of the target volume during the pre-operative treatment planning phase.

In FIG. 11, imaging system 4020 may be represented by X-ray sources 4053 and 4054 and X-ray image detectors (imagers) 4056 and 4057. In one embodiment, for example, two X-ray sources 4053 and 4054 may be nominally aligned to project imaging X-ray beams through a patient from two different angular positions (e.g., separated by 90 degrees, 45 degrees, etc.) and aimed through the patient on treatment couch 4050 toward respective detectors 4056 and 4057. In another embodiment, a single large imager can be used that would be illuminated by each X-ray imaging source. Alternatively, other numbers and configurations of imaging sources and imagers may be used.

Digital processing system 4030 may implement algorithms to register images obtained from imaging system 4020 with pre-operative treatment planning images in order to align the patient on the treatment couch 4050 within the treatment delivery system 4000, and to precisely position the radiation source with respect to the target volume.

The treatment couch 4050 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 4050 may be a component of another mechanical mechanism, such as the Axum® treatment couch or the Robocouch™ patient positioning system, both developed by Accuray Incorporated of Sunnyvale, Calif., or may be another type of conventional treatment table known to those of ordinary skill in the art.

Alternatively, treatment delivery system 4000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target. In IMRT planning, the optimization algorithm selects subsets of the main beam and determines the amount of time that the patient should be exposed to each subset, so that the prescribed dose constraints are best met. In one particular embodiment, the gantry based system may have a gimbaled radiation source head assembly.

FIG. 12 illustrates a three-dimensional perspective view of one embodiment of a non-isocentric beam delivery process. In particular, FIG. 12 depicts several radiation beams directed at a target 122. In one embodiment, the target 122 may be representative of an internal organ, a region within a patient, a pathological anatomy such as a tumor or lesion, or another type of object or area of a patient.

The illustrated radiation treatment process includes a first radiation beam 602, a second radiation beam 604, a third radiation beam 606, and a fourth radiation beam 608. Although four radiation beams 12 are shown, other embodiments may include fewer or more radiation beams. For convenience, reference to one radiation beam 602 is representative of all of the radiation beams, unless indicated otherwise. Additionally, the treatment sequence for application of the radiation beams 602 may be independent of their respective ordinal designations.

In one embodiment, the four radiation beams 602 are representative of beam delivery based on conformal planning, in which the radiation beams 602 pass through or terminate at various points within target 122. In conformal planning, some radiation beams 602 may or may not intersect, or converge, at a common point in three-dimensional space. In other words, the radiation beams 602 may be non-isocentric in that they do not necessarily converge on a single point, or isocenter. However, the radiation beams 602 may wholly or partially intersect at the target 122 with one or more other radiation beams 602.

In another embodiment, the duration of each radiation beam 602 may be determined by a beam weight that may be set by an operator or by treatment planning software. The individual beam weights may depend, at least in part, on the total prescribed radiation dose to be delivered to target 122, as well as the cumulative radiation dose delivered by some or all of the radiation beams 602. For example, if a total prescribed dose of 3500 cGy is set for the target 122, the treatment planning software may automatically predetermine the beam weights for each radiation beam 602 in order to balance conformality and homogeneity to achieve that prescribed dose.

In the depicted embodiment, the various radiation beams 602 are directed at the target 122 so that the radiation beams 602 do not intersect with the critical structures 124. However, in certain situations it may be acceptable for a number of radiation beams 602 to pass through critical structures 124 in order to realize a determined dose distribution to the target 122. In such cases, doses may be implemented which are clinically acceptable in accordance with the treatment plan and commonly used dose volume histogram values (DVH).

It should be noted that the methods and apparatus described herein are not limited to use only with medical diagnostic imaging and treatment. In alternative embodiments, the methods and apparatus herein may be used in applications outside of the medical technology field, such as industrial imaging and non-destructive testing of materials (e.g., motor blocks in the automotive industry, airframes in the aviation industry, welds in the construction industry and drill cores in the petroleum industry) and seismic surveying. In such applications, for example, "treatment" may refer generally to the application of a beam(s) and "target" may refer to a non-anatomical object or area.

Some embodiments of the present invention include various operations, which are described herein. These operations may be performed by hardware components, software, firmware, or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable storage media may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; or another type of medium suitable for storing electronic instructions. Machine-readable propagation media include electrical, optical, acoustical, or other forms of media to propagate one or more signals (e.g., carrier waves, infrared signals, digital signals, etc.).

The digital processing device(s) described herein may include one or more general-purpose processing devices such as a microprocessor or central processing unit, a controller, or the like. Alternatively, the digital processing device may include one or more special-purpose processing devices such as a digital signal processor (DSP), an application specific integrated circuit (ASIC), a field programmable gate array (FPGA), or the like. In an alternative embodiment, for example, the digital processing device may be a network processor having multiple processors including a core unit and multiple microengines. Additionally, the digital processing device may include any combination of general-purpose processing device(s) and special-purpose processing device(s).

Additionally, some embodiments may be practiced in distributed computing environments where the machine-readable medium is stored on and/or executed by more than one computer system. In addition, the information transferred between computer systems may either be pulled or pushed across the communication medium connecting the computer systems.

It should be noted that several embodiments are discussed herein in regard to a robotic, image guided radiation treatment system, the embodiments also may be used with other types of radiation treatment systems such as a gantry based radiation delivery system. It should also be noted that several embodiments are discussed herein in relation to CT imaging for ease of explanation, but some embodiments also may use other types of medical diagnostic imaging (anatomical and/or functional). For example, some embodiments may use magnetic resonance (MR), ultrasound (US), nuclear medicine (NM), positron emission tomography (PET), single photon emission computed tomography (SPECT), or another type of medical imaging. In addition, the "targets" discussed herein may include an anatomical feature(s) of a patient such as a pathological or normal anatomy and may include one or more non-anatomical reference structures. Alternatively, a target need not include an anatomical structure in embodiments outside the field of medical diagnostic imaging and patient treatment.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A computer-implemented method, comprising:
indexing a temporal sequence of images taken at different points in time in a motion cycle with a known temporal relationship, wherein each of the images depicts a spatial volume;
identifying three or more data points, wherein each of the data points describes an estimated spatial position of a selected volume element of the spatial volume in the motion cycle, wherein each of the data points corresponds to one of the images; and
calculating, using the identified data points, an estimated location of the selected volume element based on a function having a constraint which favors smooth motion of the selected volume element over time using a processing device.

2. The method of claim 1, wherein the constraint comprises a time derivative of motion of at least some of the identified data points.

3. The method of claim 1, wherein the function implements a polynomial approximation of at least some of the identified data points.

4. The method of claim 3, wherein calculating the estimated location of the selected volume element further comprises calculating a new data point consistent with the polynomial approximation.

5. The method of claim 4, further comprising replacing one of the identified data points with the new data point.

6. The method of claim 4, further comprising predicting a future data point associated with the selected volume element based on the new data point.

7. The method of claim 4, further comprising inserting the new data point between two of the identified data points.

8. The method of claim 4, further comprising developing a deformation model for a volume of interest structure within the volume of interest based on the new data point.

9. The method of claim 8, wherein the volume of interest structure comprises a target.

10. The method of claim 8, wherein the volume of interest structure comprises a critical structure.

11. The method of claim 1, wherein the motion cycle is at least a portion of a respiratory cycle of a patient.

12. The method of claim 11, wherein the temporal sequence of images comprises at least three temporally disparate images of the temporal sequence of images.

13. The method of claim 1, further comprising applying the function to one of the plurality of identified data points to generate a new spatial data point relative to a plurality of spatial data points associated with one of the images.

14. The method of claim 1, wherein calculating the estimated location of the selected volume element further comprises applying the function to the selected volume element to favor spatial continuity of the selected volume element and surrounding volume elements in a corresponding image.

15. The method of claim 1, further comprising computing a cumulative deformation field of the data points, wherein the cumulative deformation field comprises a plurality of relative deformation fields, wherein each of the plurality of relative deformation fields relates to a difference between adjacent data points of the data points.

16. The method of claim 1, further comprising computing individual deformation fields of the data points, wherein each of the individual deformation fields relates to a difference between a reference data point of the data points and another data point of the data points.

17. An apparatus, comprising:
 a data storage device to store a plurality of temporally sequential images taken at different points in time in a motion cycle with a known temporal relationship, wherein the plurality of temporally sequential images include a volume of interest structure; and
 a digital processing device coupled to the data storage device, the digital processing device to calculate a polynomial approximation of a temporal path of movement of a selected volume element of the volume of interest structure during the motion cycle using three or more of the temporally sequential images taken at three or more points in time in the motion cycle, and to calculate an estimated location of the selected volume element based on the polynomial approximation.

18. The apparatus of claim 17, wherein the digital processing device is further configured to calculate a new data point consistent with the polynomial approximation, wherein the polynomial approximation represents a deformation model of a part of the selected volume element of the volume of interest structure.

19. The apparatus of claim 18, wherein the new data point replaces one of the time points in the motion cycle.

20. The apparatus of claim 18, wherein the new data point supplements the time points in the motion cycle.

21. The apparatus of claim 17, wherein the polynomial approximation defines a continuous, non-discrete movement over time of the selected volume element of the volume of interest structure.

22. The apparatus of claim 17, wherein the data storage device is further configured to store a representation of the polynomial approximation and a new data point corresponding to the estimated location of the selected volume of interest.

23. The apparatus of claim 22, further comprising a graphical display to display a graphical representation of the polynomial approximation and the new data point corresponding to the estimated location of the selected volume of interest.

24. The apparatus of claim 23, wherein the graphical display is further configured to display a graphic representation of a plurality of identified data points associated with temporally distinct locations of the selected volume element of the volume of interest structure.

25. The apparatus of claim 17, further comprising:
 a diagnostic imaging system coupled to the digital processing device, the diagnostic imaging system to obtain the plurality of temporally sequential images; and
 a treatment delivery system coupled to the digital processing device, the treatment delivery system to deliver radiation treatment to the volume of interest structure according to a deformation model based on the polynomial approximation of the temporal path of movement of the selected volume element of the volume of interest structure.

26. A computer readable storage medium having instructions thereon, which instructions, when executed by a digital processing device, cause the digital processing device to perform the following, comprising:
 reference a temporal sequence of images taken at different points in time in a motion cycle with a known temporal relationship, wherein each of the images depicts a volume of interest;
 identify three or more data points associated with a selected volume element of the volume of interest in the motion cycle, wherein each of the data points corresponds to one of the images; and
 calculate an estimated location of the selected volume element based on a polynomial approximation of at least some of the identified data points.

27. The computer readable storage medium of claim 26, having further instructions thereon, which further instructions, when executed by the digital processing device, cause the digital processing device to perform the following, comprising calculate a new data point consistent with the polynomial approximation.

28. The computer readable storage medium of claim 27, having further instructions thereon, which further instructions, when executed by the digital processing device, cause the digital processing device to perform the following, comprising replace one of the identified data points with the new data point.

29. The computer readable storage medium of claim 27, having further instructions thereon, which further instructions, when executed by the digital processing device, cause the digital processing device to perform the following, comprising predict a future data point associated with the selected volume element based on the new data point.

30. The computer readable storage medium of claim 27, having further instructions thereon, which further instructions, when executed by the digital processing device, cause the digital processing device to perform the following, comprising develop a deformation model for a volume of interest structure within the volume of interest based on the new data point.

31. The computer readable storage medium of claim 26, having further instructions thereon, which further instructions, when executed by the digital processing device, cause the digital processing device to perform the following, comprising apply a spatial smoothing function to one of the plurality of identified data points to generate a new spatial data point relative to a plurality of spatial data points associated with one of the images.

32. The computer readable storage medium of claim 26, having further instructions thereon, which further instructions, when executed by the digital processing device, cause the digital processing device to perform the following, comprising compute a cumulative deformation field of the data points, wherein the cumulative deformation field comprises a plurality of relative deformation fields, wherein each of the plurality of relative deformation fields relates to a difference between adjacent data points of the data points.

33. The computer readable storage medium of claim 26, having further instructions thereon, which further instructions, when executed by the digital processing device, cause the digital processing device to perform the following, comprising compute individual deformation fields of the data points, wherein each of the individual deformation fields relates to a difference between a reference data point of the data points and another data point of the plurality of data points.

34. An apparatus, comprising:

means for identifying a deformation model for a selected volume element over time, wherein the deformation model comprises three or more data points corresponding to a temporal sequence of images taken at different points in time in a motion cycle with a known temporal relationship, wherein each of the data points describes an estimated spatial position of the selected volume element in the motion cycle; and means for modifying the deformation model based on an assumption that the selected volume element moves along a continuous path over time.

35. The apparatus of claim 34, further comprising means for approximating the deformation model.

36. The apparatus of claim 34, further comprising means for generating a new data point which is consistent with an approximation of the deformation model.

37. The apparatus of claim 36, further comprising means for replacing one of the data points of the identified deformation model.

38. The apparatus of claim 36, further comprising means for predicting a future data point of the identified deformation model.

* * * * *